US006584833B1

(12) United States Patent
Jamison et al.

(10) Patent No.: US 6,584,833 B1
(45) Date of Patent: Jul. 1, 2003

(54) APPARATUS AND METHOD FOR ANALYZING WELL FLUID SAG

(75) Inventors: Dale E. Jamison, Humble, TX (US); Robert J. Murphy, Jr., Kingwood, TX (US)

(73) Assignee: Halliburton Energy Services, Inc., Duncan, OK (US)

( * ) Notice: Subject to any disclaimer, the term of this patent is extended or adjusted under 35 U.S.C. 154(b) by 0 days.

(21) Appl. No.: 10/162,795

(22) Filed: May 30, 2002

(51) Int. Cl.$^7$ ............................................. G01N 33/40
(52) U.S. Cl. .................... 73/61.63; 73/54.39; 73/54.37; 73/54.28
(58) Field of Search ........................... 73/53.01, 54.01, 73/54.02, 54.05, 54.28, 54.37, 54.39, 61.41, 61.43, 61.63

(56) References Cited

U.S. PATENT DOCUMENTS

| | | | | |
|---|---|---|---|---|
| 2,845,793 A | * | 8/1958 | Cardwell, Jr. | 73/61.65 |
| 3,289,467 A | * | 12/1966 | Parker et al. | 73/61.63 |
| 3,371,523 A | * | 3/1968 | Crouch et al. | 73/65.03 |
| 4,474,056 A | * | 10/1984 | O'Brein | 73/61.69 |
| 4,823,594 A | * | 4/1989 | Gray | 73/54.01 |
| 5,086,646 A | | 2/1992 | Jamison et al. | 73/65 |
| 5,763,766 A | * | 6/1998 | Robinson | 73/54.33 |
| 5,987,969 A | * | 11/1999 | Joseph et al. | 73/53.01 |
| 6,240,770 B1 | * | 6/2001 | Raffer | 73/54.28 |
| 6,330,826 B1 | | 12/2001 | Meeten | 73/152.62 |

OTHER PUBLICATIONS

AADE 01–NC–HO–51,"Prevention of Dynamic Sag in Deepwater Invert Emulsion fluids," C. Aldea, F.B. Growcock, L.J. Lee and J.E. Friedheim, AADE 2001 National Drillin gConference, held in Houston, Texas ( Mar. 27–29, 2001).

SPE 56636, "Correlation of Ultra–low Shear Rate Viscosity and Dynamic Barite Sag in Invert–Emulsion Drilling Fluids," William Dye, Terry Hemphill, William Gusler and Gregory Mullen, 1999 SPE Annual Technical Conference and Exhibition held in Houston, Texas (Oct. 33–6, 1999).

* cited by examiner

Primary Examiner—Helen Kwok
Assistant Examiner—David Rogers
(74) Attorney, Agent, or Firm—Craig W. Roddy; Karen B. Tripp

(57) ABSTRACT

An apparatus and method are disclosed for measuring or analyzing dynamic and static sag caused by settling of weighting materials in drilling fluids or other solids bearing fluid. The apparatus comprises a tube and shear shaft assembly that allows for a controlled rate of shear to be applied to a sample of the fluid for testing. During a test, the assembly is placed on a pivotal holder at an angle. The assembly has pistons at the pivot center of the assembly which accommodate expansion and contraction of the test fluid due to changes in temperature and pressure, thereby allowing the test fluid to be heated, cooled and pressurized to simulate subterranean wellbore conditions without changing the center of mass of the test fluid. When weight material settles down the inclined assembly, the center of mass of the assembly changes resulting in changing torque or moment about the pivotal holder. The resultant moment is measured by energizing external coils arranged to provide a uniform magnetic field. The bulk average settling rate is determined using the measured coil current rate of change.

20 Claims, 7 Drawing Sheets

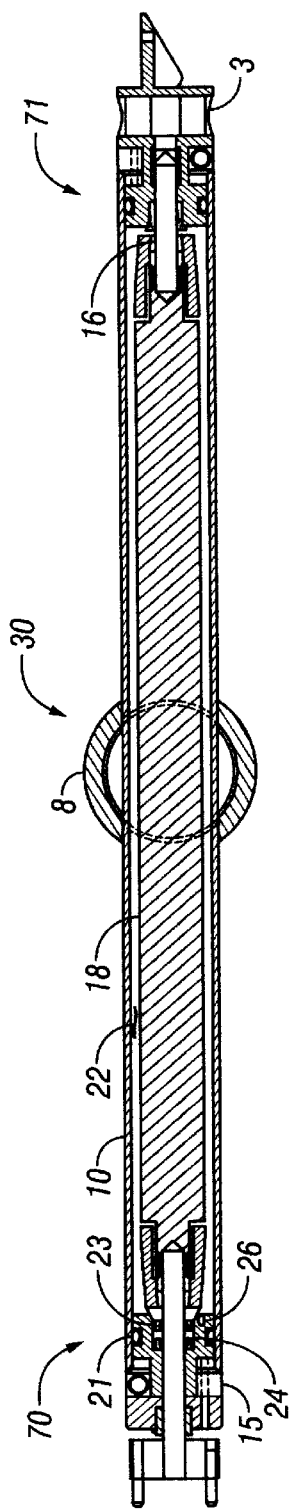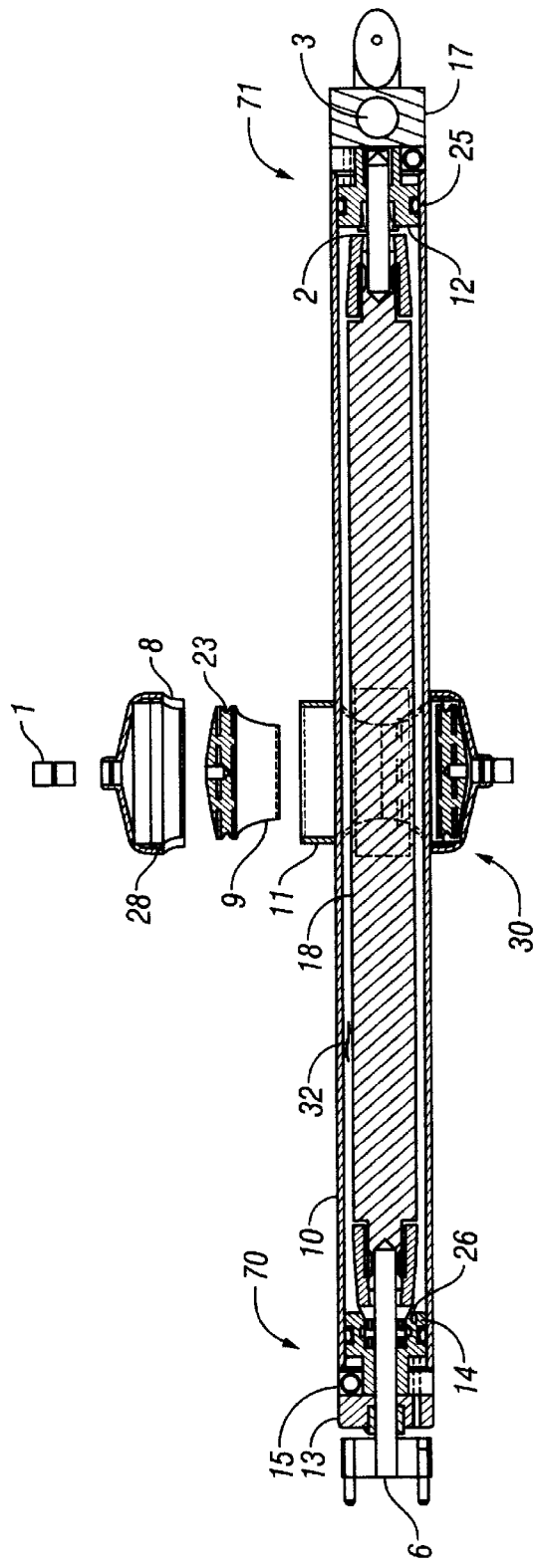
FIG. 2A
FIG. 2B

APPARATUS AND METHOD FOR ANALYZING WELL FLUID SAG

BACKGROUND OF THE INVENTION

1. Field of the Invention

The present invention relates to apparatuses and methods for monitoring, measuring, or analyzing the sag of a weight material in a drilling fluid.

2. Description of Relevant Art

A drilling fluid, or "mud" which a drilling fluid is also often called, is a specially designed fluid that is circulated in a wellbore or borehole as the wellbore is being drilled in a subterranean formation to facilitate the drilling operation. The various functions of a drilling fluid include removing drill cuttings from the wellbore, cooling and lubricating the drill bit, aiding in support of the drill pipe and drill bit, and providing a hydrostatic head to maintain the integrity of the wellbore walls and prevent well blowouts. Specific drilling fluid systems are selected to optimize a drilling operation in accordance with the characteristics of a particular geological formation.

A drilling fluid typically comprises water and/or oil or synthetic oil or other synthetic material or synthetic fluid as a base fluid, with solids in suspension. A non-aqueous based drilling fluid typically contains oil or synthetic fluid as a continuous phase and may also contain water dispersed in the continuous phase by emulsification so that there is no distinct layer of water in the fluid. Such dispersed water in oil is generally referred to as an invert emulsion or water-in-oil emulsion.

A number of additives may be included in such drilling fluids and invert emulsions to enhance certain properties of the fluid. Such additives may include, for example, emulsifiers, weighting agents, fluid-loss additives or fluid-loss control agents, viscosifiers or viscosity control agents, and alkali. Weighting agents are commonly added to increase the density of the fluid. Barite is a typical weighting agent, although other minerals are also common.

Suspensions of solids in non-vertical columns are known to settle faster than suspensions in vertical ones, due to the "Boycott effect." This effect is driven by gravity and impeded by fluid rheology, particularly non-Newtonian and time dependent rheology. Manifestation of the Boycott effect in a drilling fluid is known as "sag." Sag may also be described as a "significant" variation in mud density (>0.5 lbm/gal) along the mud column, which is the result of settling of the weighting agent or weight material and other solids in the drilling fluid.

Drilling fluid in deviated wellbores can exhibit the Boycott effect, and sag, in both static and dynamic situations. In this context, static is a totally quiescent fluid state, such as when drilling has ceased; dynamic is any situation where the fluid is exposed to a shear stress, such as for example during drilling. Sag can result in formation of a bed of the weighting agent on the low side of the wellbore, and stuck pipe, among other things. In some cases, sag can be very problematic to the drilling operation and in extreme cases may cause hole abandonment.

U.S. Pat. No. 5,086,646, issued Feb. 11, 1992 to Jamison et al., teaches an apparatus and method for analyzing well fluid sag, particularly static sag. Dynamic sag, however, can be more than an order of magnitude greater than static sag. As directional drilling and deviated wellbores become more common if not the norm in the oil and gas industry, more and improved apparatuses and methods are needed to measure or analyze dynamic sag.

SUMMARY OF THE INVENTION

An apparatus and method are provided for measuring or analyzing dynamic sag as well as static sag in a drilling fluid or other solids bearing fluid. The apparatus of the invention comprises a tube or other elongated container and a rotatable, concentric inner cylinder or shear shaft. The tube and shear shaft are assembled together such that the annulus region between them is capable of holding fluid, especially fluid to be tested. Said shear shaft is preferably free to rotate, and its rate of rotation is preferably controllable. A rotator or other means is provided for rotating the shaft. For example, rotation of the shaft might be provided by coupling a motor or motor drive mechanism to an end of the tube and shear shaft assembly. Preferably, the motor should be engageable and disengageable from the shaft so that the motor drive mechanism can be disengaged from the assembly during the measurement process to preferably avoid any interference with the measurement.

The apparatus of the invention further comprises a holder or housing, such as a pressure vessel, for holding the assembly comprising the tube and the shear shaft such that the axis of the tube and shear shaft is positioned at an angle to vertical, such as about 45 degrees, for example. Preferably, said holder may also be filled with fluid, such as a pressurization fluid, in a manner that immerses or covers the tube and shear shaft assembly. Preferably, such holder fluid can be heated and pressurized to simulate conditions in a wellbore penetrating a subterranean formation. At least one seal or other isolator isolates or otherwise keeps separate or apart the test fluid and the pressurization fluid. Such seal is preferably positioned on at least one end of the tube, and in one embodiment may preferably be positioned on the same end of the tube (or tube and shear shaft assembly) as a coupler for attaching a motor drive mechanism to the shear shaft (or to the tube and shear shaft assembly). The top or higher end of the tube and shear shaft assembly, which is preferably the opposite end (rather than the same end) from any motor drive mechanism, contains one or more magnets, preferably rare-earth permanent magnets.

Further, the apparatus of the invention comprises a support for the tube and shear shaft assembly preferably positioned at or near the center of the assembly. The support should allow rotation, preferably frictionless rotation, about the horizontal axis normal to the tube and shear shaft assembly axis. The support should also be comprised of (or be associated with) an electrically conductive medium. A preferred example of a particularly suitable support comprises two cross-spring pivots.

At least one and preferably two pistons may be included in the apparatus on the same axis as the pivots or other support. The pistons accommodate expansion and contraction of the test fluid due to changes in temperature and pressure, thereby allowing the test fluid to be heated, cooled and pressurized without changing the center of mass of the test fluid relative to the pivot axis due to thermal expansion or fluid compressibility.

Energizing external coils, preferably in a Helmholtz coil configuration, are arranged external to the holder or pressure vessel, at the magnet end of the tube and shear shaft assembly to provide a magnetic field, preferably a uniform magnetic field. Coil control circuitry is associated with the energizing coils to enable detection and measurement of change in torque or moment about the pivot axis of the assembly. Any detector capable of detecting and measuring change in torque or moment about a central axis or pivot point could be substituted for the coils and coil circuitry, provided the detector is sufficiently sensitive to detect sag.

In the method of the invention, the apparatus of the invention or another apparatus capable of conducting the steps of the method is used for measuring or analyzing the dynamic and/or static sag of a fluid such as a drilling fluid or other fluid used in drilling, cementing, casing, or workover operations in a subterranean wellbore. As used herein, the term "drilling fluid" shall be understood to include fluids used in any of these downhole operations. In the method, when measuring or analyzing dynamic sag, shear is applied to a test sample of the fluid at a controlled rate and the rate of sag or settling by the weighting agent (or other material) in the fluid is measured. When measuring or analyzing static sag, shear is not applied to the test sample of the fluid—the shear shaft is not rotated—and the rate of sag or settling by the weighting agent (or other material) in the fluid is measured.

During either a dynamic or static test, the fluid is in an inclined tube assembly. Settling of the weighting agent or material causes the center of mass to change, which in turn causes a change in the torque or moment about the pivots or other holders for the tube and shear shaft assembly. The resultant moment is preferably measured by energizing external coils such that the upper end of the tube (which comprises a permanent magnet) and shear shaft assembly is driven back to its initial zero position. This zero position is initially detected by closing a circuit attached to a stationary contact and to the tube and shear shaft assembly (preferably at the upper end). The coil control circuitry is a self-integrating error accumulator that automatically drives the coil current. As the coil is precisely energized, it provides a force on the permanent magnet, which repositions the tube and shear shaft assembly at zero position. When compensated for the minor effects of temperature and other effects, the coil current is proportional to the imbalance of the tube and shear shaft assembly. The greater the imbalance, the greater the coil current, indicating the greater the amount of sag in the fluid. Measurement of the sag may then be calculated as a function of the current over time.

BRIEF DESCRIPTION OF THE FIGURES

FIG. 2(a) is a side view of the tube and shear shaft assembly portion of a preferred apparatus of the invention.

FIG. 2(b) is a top view of the tube and shear shaft assembly shown in FIG. 2(a).

DETAILED DESCRIPTION OF PREFERRED EMBODIMENTS

Figure 1:
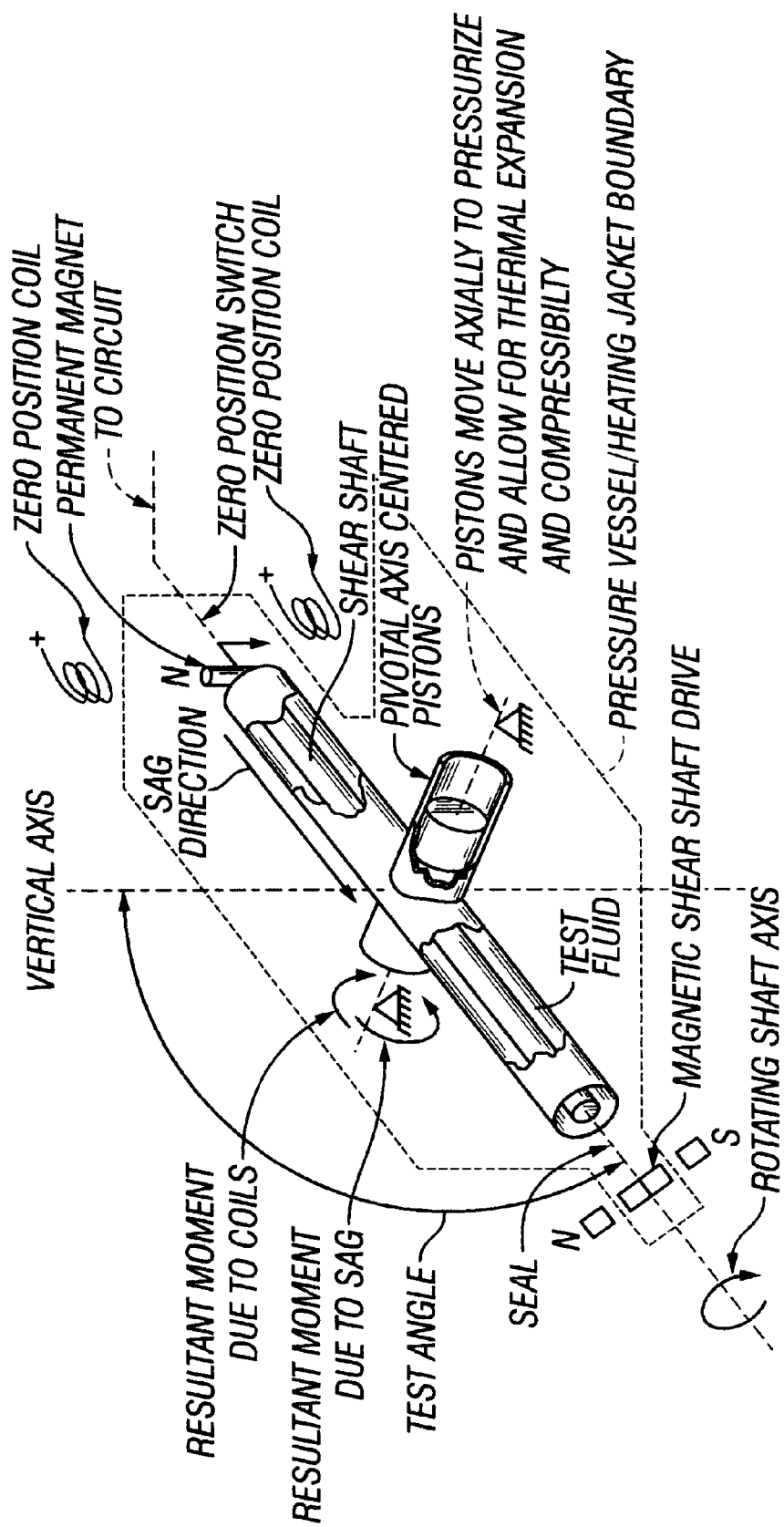
FIG. 1 is a schematic drawing of a preferred apparatus of the invention.

The present invention provides a method for measuring or analyzing the rate of sag or settling of a weighting agent or material in a drilling fluid or other solids bearing fluid. The present invention also provides an apparatus particularly suited for carrying out the method of the invention. An advantage of the present invention is that it can be used to measure dynamic sag as well as static sag. The invention is useful not only in determining drilling fluid properties and in designing, developing and/or selecting a drilling fluid, but also in gaining insight into the mechanism of sag for use in future drilling modeling software.

The present invention provides the beneficial capability of applying uniform shear to a test fluid (i.e., a sample of fluid containing weighting material for sag testing) at a controlled rate. Such a controlled rate approximates the shear a fluid is likely to encounter in a drilling operation, and simulates the shear the drilling fluid encounters in the well bore annulus, where the drill cuttings are transported to the surface. Thus, the invention affords closer approximation to the shear forces that a fluid is expected to actually encounter in a well than prior art devices. Such approximation is made more realistic by putting the apparatus under pressure and temperatures expected to be encountered in a wellbore penetrating a subterranean formation. Moreover, the capability of applying shear to a test fluid enables the measurement or analysis of dynamic sag as well as static sag.

FIGS. 1, 2a, 2b, 3, and 7 illustrate an exemplary embodiment of an apparatus according to the present invention. Referring to these figures, and particularly to FIGS. 2(a) and (b), the illustrated apparatus has a tube 10 with a concentric inner cylinder or shear shaft 18 positioned in the tube in a manner that allows the shaft 18 to rotate freely. The shear shaft 18 is centered and supported by a co-axial drive shaft 6 on one end, and a positioning shaft 16 on the other, and their corresponding bearings 2, in end caps 13 and 17. The embodiment shown has multi-piece closures 70, 71, made up of pieces 13, 15, 14 and 12, 15, 17 respectively at each end of the assembly 30. Piece 15 comprises a locking function. The apparatus could alternatively have a single piece closure at each end, preferably that includes a locking function.

The shear shaft 18 and the tube 10 together comprise an assembly 30. A rotator or other means or mechanism for rotating the shaft, such as a motor (not shown) is coupled to (or otherwise attached or associated with) the shaft 18 by means of drive shaft 6 to rotate the shaft 18. Preferably, such rotator can be easily adjusted to rotate the shaft 18 at different rotary speeds as desired and can also be easily removed, disengaged or otherwise turned off as desired. In the preferred embodiment, referring to FIG. 3, the rotator is a magnetic rotor 48, driven by means of a rotating magnetic field external to the pressure vessel 35. The specific speeds are preferably between about 1 and about 100 rpm. The magnetic rotor is coaxial with the assembly 30, and supported by bearings inside of the end 141 of pressure vessel 35. The magnetic rotor is preferably disengaged from the shaft 18 during measurements for sag to avoid interference of the rotor with the measurements. The measurements are then taken while dynamic sag conditions are still present. The magnetic rotor may be re-engaged for further application of shear rate to the fluid, and then disengaged for measurements, with this process being continually repeated, preferably for the entire test.

The assembly 30 has an annular hollow space 32 as shown in FIGS. 1, and 2(a) and (b) between the shaft 18 and the interior wall of the tube 10 for containing fluid to be tested in the apparatus. Closures 70 and 71 as shown in FIGS. 2(a) and (b) prevent the test fluid from leaking from the assembly 30. On at least one end of the assembly 30 and preferably on both ends, the closures are removable for filing the assembly 30 or at least the space 32 with test fluid. The closures 70 and 71 may also preferably have seals 20, 21, 24, 25, and 26 to further prevent leakage and to provide a tight fit and closure to the assembly 30.

Figure 3:
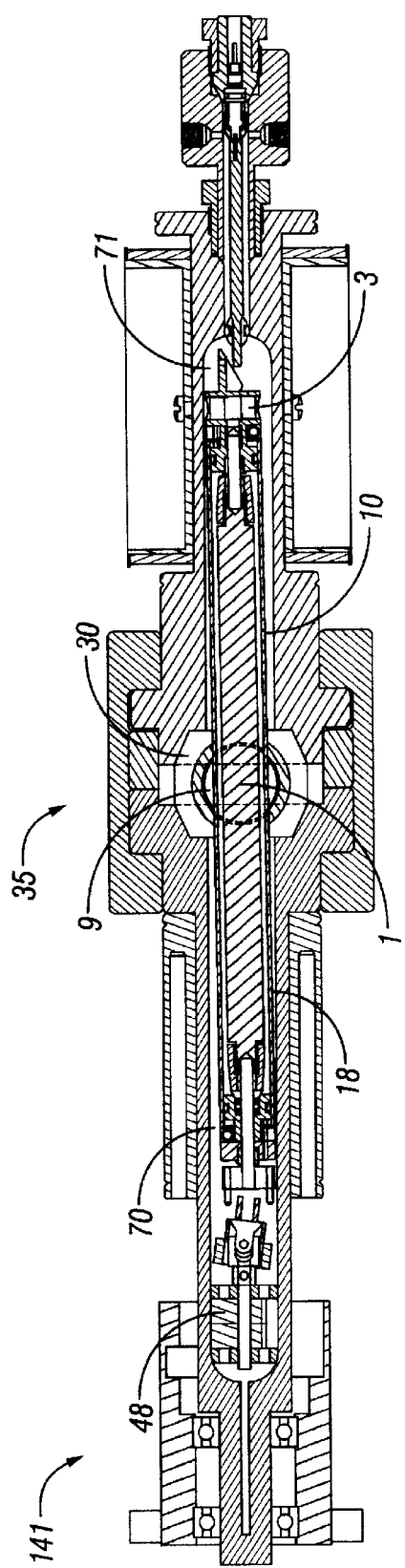
FIG. 3 is a side view of a preferred apparatus of the invention showing the tube and shear shaft assembly (also shown in FIGS. 2(a) and (b)) positioned in a holder.

As shown in FIG. 3, the assembly 30 is housed in an outer pressure vessel 35 which may be filled with a pressurization fluid to immerse the sealed assembly 30. The pressurization fluid is pressurized by means of an external pump and supply (not shown), to maintain the desired test pressure. Referring to FIGS. 2(a) and (b), seal 20 in the end cap 14 should prevent mixing of the pressurization fluid with the test fluid, past the drive shaft 6. Two cross-spring pivots 1 located inside said pressure vessel 35 provide support for the assembly 30 at or near the assembly's center. These pivots 1 allow the assembly 30 to be tilted through a small angle (less than or equal to about 10 degrees), within the outer pressure vessel 35. In the preferred embodiment, the pivots 1 should be comprised of an electrically conductive medium or should otherwise be made electrically conductive.

As shown in FIG. 2(b), two floating pistons 9 are positioned on the same axis as the pivots 1 by housing 11. Housing 11 is fastened to tube 10 by a leak-proof means, preferably soldered. The pistons 9 are sealed by sliding seals 23. One side of each piston 9 is in free communication with the test fluid in the annular hollow space 32 by means of a port through the wall of the tube 10. The other side of each piston 9 is in free communication with the pressurization fluid immersing the assembly 30. These pistons 9 are free to move so that the pressure of the test fluid in the gap 32 is essentially the same as the pressure of the pressurization fluid surrounding the assembly 30. The axial motion of the pistons 9, and the test fluid that the pistons 9 retain, do not change the balance of the assembly 30 because such axial motion remains at the pivot center of the assembly 30. This piston motion compensates for the volume changes of the test fluid as the test fluid is heated, cooled and pressurized, without changing the center of mass of the test fluid relative to the pivot axis due to thermal expansion or fluid compressibility.

Figure 7:
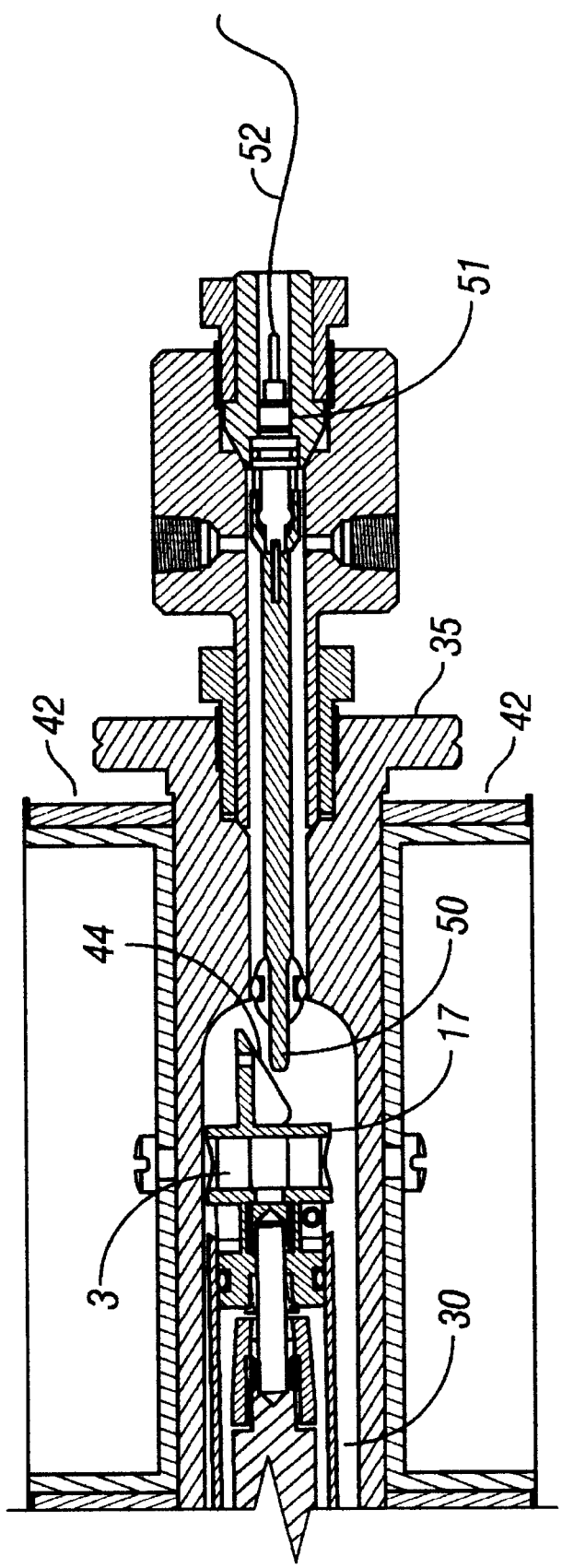
FIG. 7 is a side view of the top end of a preferred apparatus of the invention, in cross section, showing the permanent magnets, coils and the zero position contacts.

End cap 17 contains at least one permanent rare earth magnet 3, as shown in FIGS. 2(b) and 7. Referring further to FIG. 7, external coils 42 are arranged in a Helmholtz coil configuration to provide a uniform magnetic field about the permanent magnet 3. This field acts on the rare-earth permanent magnet 3 in endcap 17. When the end of the contact wire 44, attached to end cap 17, contacts a stationary insulated contact 50 in the end of pressure vessel 35, a circuit is closed that detects the "zero" position for pivoting tube assembly 30. The contact wire 44 is preferably made of a corrosion resistant conductive material, such as the metal tungsten. The stationary contact 50 is also preferably made of, or coated with, a corrosion resistant conductive material, such as gold. The stationary contact 50 passes through an electrically insulated pressure seal 51 in the end of the pressure vessel 35. An electrically insulated wire 52 conveys the contact zero position current to the control circuitry.

Figure 5:
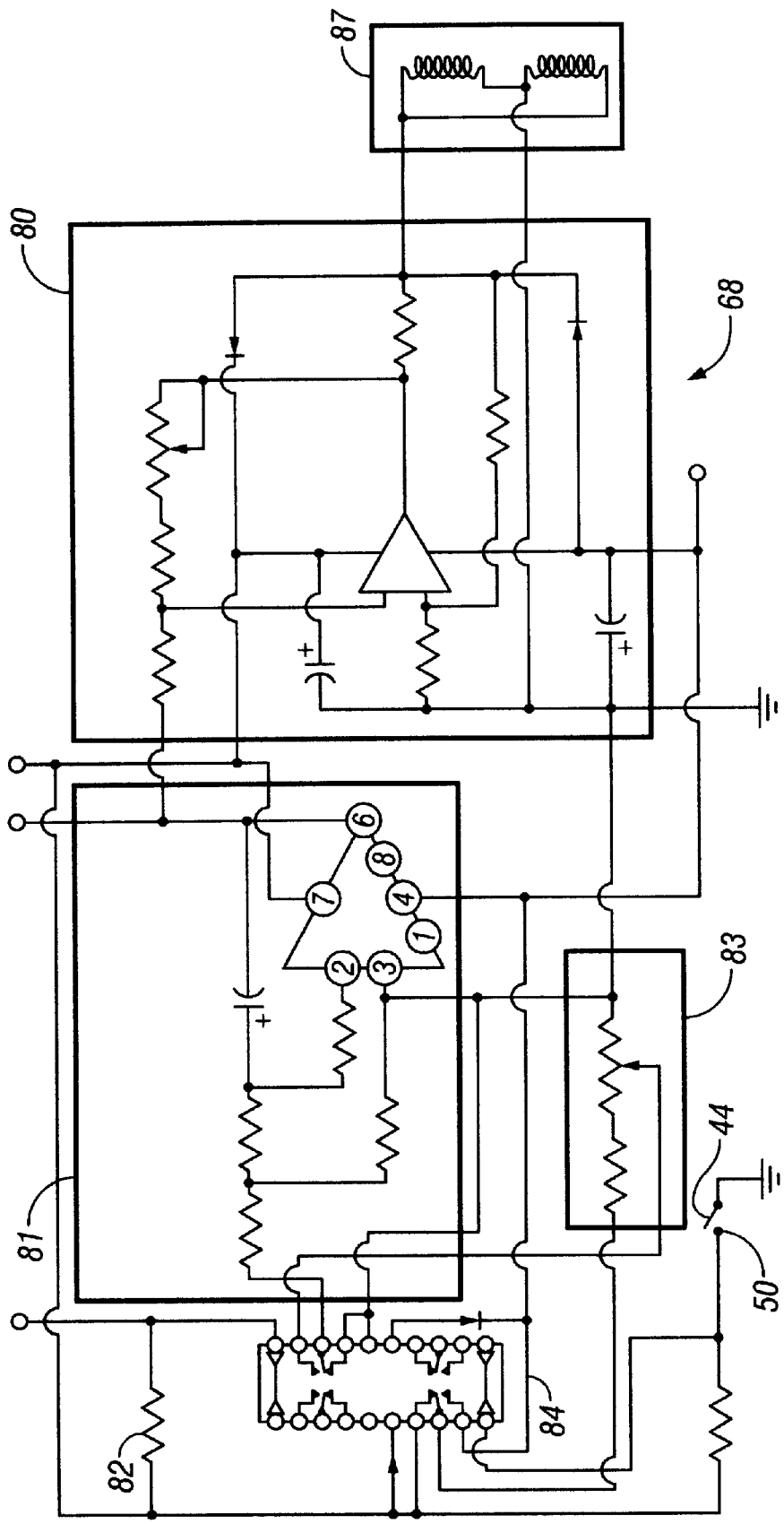
FIG. 5 is an example control schematic for a circuit of a preferred apparatus of the invention effecting a self-integrating error accumulator to automatically drive the coil current for detecting and measuring sag.
Figure 6:
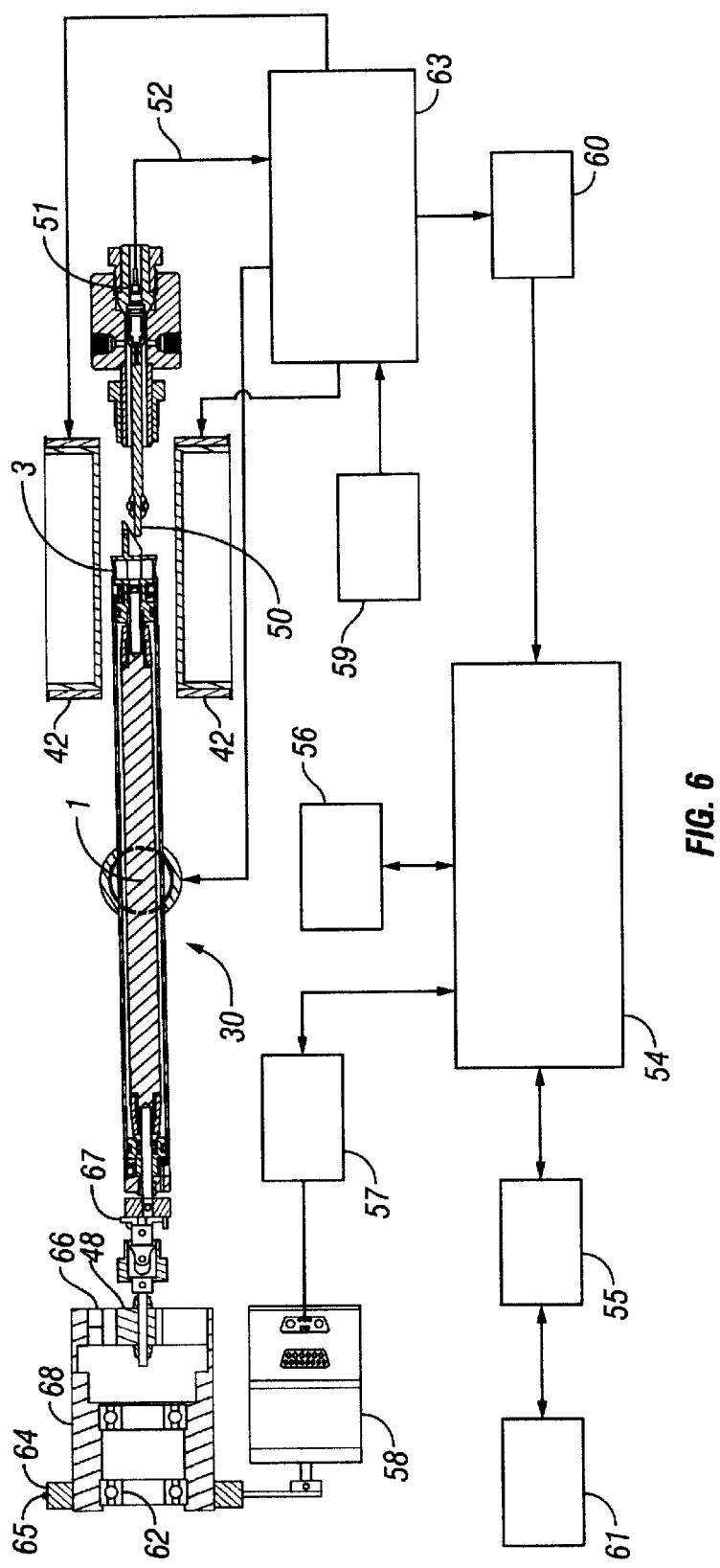
FIG. 6 is a block diagram of the current path used in detecting and measuring sag with a preferred apparatus of the invention shown in FIGS. 3 and 7.

In operation, i.e., when a test is underway, the coil control circuitry, diagramed for example in FIG. 5, is a self-integrating error accumulator that automatically drives the coil current. The coil control circuitry 68 is made up of an enable/hold circuit 82, multiplying integrator circuit 81, integration rate adjustment circuit 83, integration direction circuit 84 and coil driver circuit 80. The coil driver circuit connects to coils 42. The primary input is the state of the switch made up of contact wire 44 and stationary contact 50. The primary outputs of the coil control circuitry 68 are a current of the right magnitude and polarity to position the tube assembly at the zero position, and a voltage that is proportional to the coil current. The current path is diagramed for example in flow chart form in FIG. 6. Referring to FIGS. 6 and 7, as the coil is precisely energized, it provides a force on the permanent magnet 3, which repositions the assembly 30 to zero position, approximately co-axial with the outer pressure vessel 35. In the zero position, the assembly 30 does not touch the walls of the outer pressure vessel 35. The coils 42 will be energized so that the moving contact wire 44 is kept just barely in contact with the stationary contact 50 of the pressure vessel 35 to maintain the zero position. Electrical feed-through 51 and wire 52 convey the current of the circuit to control circuitry 68. The zero position feedback circuit is completed from the control circuitry 68 through electrically conductive pivot 1, and through the electrically conductive tube assembly 30, to contact wire 44.

In alternative embodiments of the apparatus of the invention, in lieu of the preferred electrical contacts, any other sensor method that accurately detects the position of assembly 30 could be used in the control of the coils 42 to maintain the zero position.

Referring further to FIG. 6, digital computer 54 controls most of the functions of the apparatus of the invention during a test. It sends the appropriate commands to temperature controller 56, pressure controller 55, and servo motor controller 57. The pressure controller controls the action of pump 61 to maintain the test pressure. The servo motor controller 57 controls the speed of servomotor 58. The rotation of servomotor 58 is transmitted by means of belt 65 to pulley 64 to rotate magnet drive housing 63. The magnet drive housing 63 is supported on the outside of the pressure vessel (not shown in FIG. 6) by means of ball bearings 62. The magnet drive housing 63 holds permanent magnets 66, which couple magnetically to the magnetic rotor 48, inside the pressure vessel. The disengageable coupling 67 connects the magnetic rotor 48 to tube assembly 30. Power supply 59 provides electrical power for the coil control circuitry 68. A voltage proportional to the coil 42 current is sent from the coil control circuitry 68 to an analog-to-digital converter 60, and then to the digital computer 54.

When all coil current measurements are made when the rotator (or rotational drive) for the shear shaft 18 is mechanically disengaged, and assembly 30 is in the zero position, the force required to flex the cross-spring pivots 1 and to maintain the slight electrical contact is constant and can thus be disregarded. The combination of the flexural pivot and the coil re-positioning technique is sometimes called a force re-balance system.

The bulk average settling rate for the test fluid is related to the rate of change of the measured coil current (at zero position). In the preferred embodiment of the present invention, the current to the coils 42 is measured and recorded at regular intervals by a computer controlled system. The same system preferably controls the pressure, temperature, and the shear rate for the test.

Figure 4:
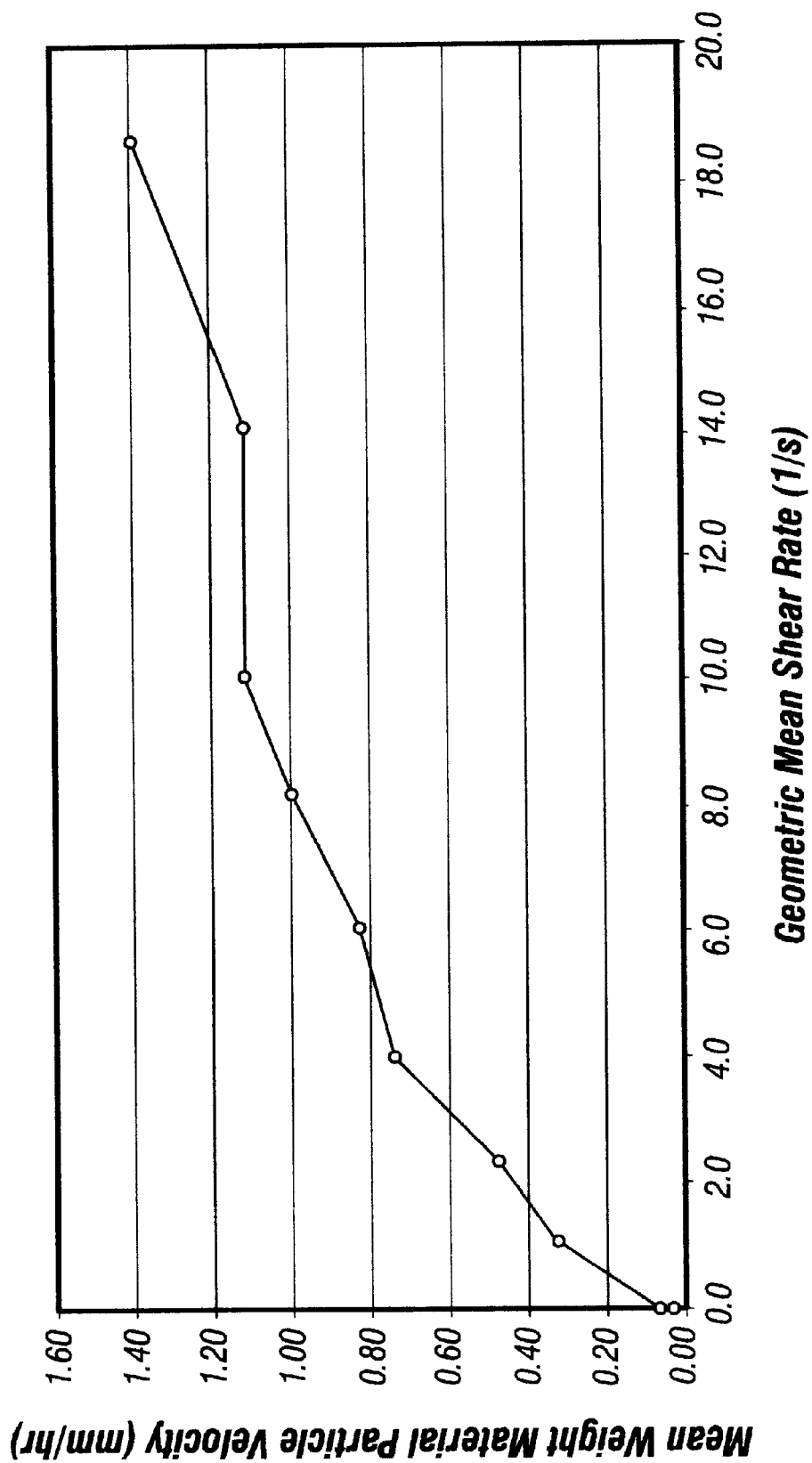
FIG. 4 is a graph showing typical sag data taken with an apparatus of the invention, showing the settling rate of Barite in a drilling fluid as a function of shear rate.

The resulting body of data, as a function of time, can be analyzed in several different ways, as would be known to those skilled in the art. One example is to express the data as the distance that the center of gravity shifts, knowing only the density of the sample fluid and the volume. Other methods are possible. Generally, it is often desirable to relate in some way a parameter of the fluid test sample indicative of sag of the sample over time. FIG. 4 shows a plot of test results with a preferred apparatus of the invention. The plot provides dynamic sag data showing the rate of settling by Barite in a sample drilling fluid as a function of shear rate applied to the sample.

In the method of the invention, an apparatus of the invention or an apparatus with similar capabilities or features is used to measure or analyze dynamic sag and/or static sag of a fluid such as a drilling fluid or mud containing weighting materials and/or other solid particles. In the method, a sample of the fluid to be tested is placed in a testing apparatus with a central pivot point resting in an inclined position. The fluid is preferably placed under pressure and at a temperature simulating the environment in which the fluid will be used, such as subterranean wellbore conditions. Such pressurization and temperature should not noticeably affect the center of mass of the fluid in the apparatus relative to its pivot axis. If dynamic sag is to be tested, the fluid is subjected to shear, preferably at a controlled rate during the test. If static sag is to be tested, the fluid is allowed to sit without disturbance during the test. In either type test, settling of solid particles in the test fluid—the sag phenomenon—causes the center of mass of the fluid in the testing apparatus to change, which in turn causes a change in the torque or moment about the central pivot point of the apparatus. The resultant moment is measured over time and correlated to the amount of sag experienced with the fluid. A preferred method of measuring the resultant moment is with energizing external coils and a self-integrating error accumulator that drives current, particularly or preferably in conjunction with or as part of a force re-balance system.

The foregoing description of the invention is intended to be a description of preferred embodiments. Various changes in the detail of the described apparatus and method can be made without departing from the intended scope of this invention as defined by the appended claims.

We claim:

1. An apparatus for measuring or analyzing sag in a drilling fluid, or other solids bearing fluid, said apparatus comprising:
   an assembly comprising an elongate container and a rotatable, concentric inner cylinder, separated by an annulus for containing said fluid;
   a rotator for rotating said shaft;
   a horizontal pivoting support for said assembly, near its geometric center, forming a central pivot axis;
   a housing for said assembly and said pivoting support for immersing said assembly in pressurization fluid and for holding said container in an inclined position;
   at least one piston in communication with said test fluid and said pressurization fluid along said central pivot axis;
   at least one seal for keeping said test fluid and said pressurization fluid separate;
   a detector for detecting or measuring change in torque or moment about said central pivot axis at a constant angle of incline.

2. The apparatus of claim 1 wherein said elongate container is a tube and said cylinder is a shear shaft and wherein said assembly has at least one removable end closure.

3. The apparatus of claim 1 wherein said pressurization fluid may be heated above room temperature or chilled below room temperature.

4. The apparatus of claim 1 wherein said rotator is a magnetic rotor driven by a rotating magnetic field.

5. The apparatus of claim 4 wherein said rotator is capable of controllably rotating said shaft such that said shaft imparts a controlled rate of shear to said test fluid.

6. The apparatus of claim 1 wherein said detector comprises a pair of contacts to sense a reference position and energized external coils acting on a movable magnetic.

7. The apparatus of claim 6 wherein said detector further comprises coil control circuitry;
   said elongate container has at least one magnet in one end and said pivot is comprised of or associated with a conductive material.

8. An apparatus for measuring or analyzing dynamic sag in a drilling fluid, or other solids bearing fluid, said apparatus comprising a tube with a rotatable, concentric inner shear shaft separated from said tube by an annulus for containing test fluid, wherein said tube is housed in a pressurizable vessel and positioned on an incline with a central pivotal axis;
   said apparatus further comprising at least one magnet at one end of said tube, which is positioned in proximity to energizing external coils such that a magnetic field is generated, and having coil control circuitry associated therewith for detecting change in the moment about said pivotal axis, said apparatus having further associated therewith a rotator for rotating said shaft and imparting a controlled rate of shear to said test fluid.

9. The apparatus of claim 8 further comprising temperature controls for said pressurization vessel for heating or chilling said test fluid.

10. The apparatus of claim 8 wherein said magnetic field is uniform.

11. A method for measuring or analyzing dynamic sag in a fluid, said method comprising:
    providing a sample of said fluid in an elongated container inclined on a central pivotal axis;
    pressurizing said container and heating or chilling said container to simulate fluid environmental conditions;
    accommodating expansion and contraction effects of said pressure and temperature on said fluid in said container so that the center of mass of the fluid relative to said central pivotal axis is not changed due to said effects;
    imparting a controlled rate of shear to said fluid;
    monitoring the torque or moment about said central pivotal axis;
    detecting and measuring any change in said torque or moment over time; and
    relating said measurements to sag in the fluid.

12. The method of claim 11 wherein said fluid is a drilling fluid comprising weighting materials and said environment is a wellbore penetrating a subterranean formation.

13. A method for measuring or analyzing sag in a drilling fluid, said method comprising:
    providing a sample of said fluid in a elongated container with an inner, rotatable shear shaft and an annulus region in between for containing said fluid sample;
    coupling or engaging a rotator to said shaft for controllably rotating said shaft;
    immersing said container in temperature controlled pressurization fluid;
    inclining said continuously immersed container on a central pivotal axis with adjacent pistons to accommodate test fluid expansion and contraction due to any temperature adjustments and pressurization;

rotating said shaft and imparting a controlled rate of shear to said fluid;

detecting and measuring any change in moment about said pivotal axis over time;

relating said measurements to quantify sag in said fluid.

14. The method of claim 13 wherein a force re-balance system is used to detect and measure said change in moment.

15. The method of claim 13 wherein said temperature controlled pressurization fluid simulates subterranean formation temperature and pressure.

16. A method for analyzing the dynamic sag phenomenon in a drilling fluid, or other solids bearing fluid, in a subterranean borehole, said method comprising:

placing a sample of said fluid in an apparatus positioned on an incline with a pivotal support located at a central axis of said apparatus about which the apparatus can rotate or pivot; wherein the apparatus is associated with control circuitry and a self-integrating error accumulator that drives current such that the current adjusts to prevent said rotation about said pivot;

applying pressure and adjusting temperature to approximate the pressure and temperature the fluid would encounter in said borehole;

applying a controlled shear rate to said sample in said apparatus;

monitoring and measuring the current at said pivot axis over time; and relating change in current to sag in said sample fluid.

17. The method of claim 16 wherein said pivotal support is comprised of an electrically conductive material.

18. The method of claim 16 further comprising accommodating expansion and contraction of said sample fluid due to said pressure and temperature without changing the center of mass of the sample fluid relative to said pivot axis.

19. The method of claim 16 wherein said shear rate is applied by rotation of a shaft in said apparatus in contact with said fluid sample.

20. The method of claim 19 wherein said rotation is caused by a magnetic rotor.

* * * * *